US012285359B2

(12) United States Patent
Voigt et al.

(10) Patent No.: US 12,285,359 B2
(45) Date of Patent: Apr. 29, 2025

(54) EYE SURGERY SURGICAL SYSTEM AND COMPUTER IMPLEMENTED METHOD FOR PROVIDING THE POSITION OF AT LEAST ONE TROCAR POINT

(71) Applicant: Carl Zeiss Meditec AG, Jena (DE)

(72) Inventors: Christian Voigt, Abtsgmuend (DE); Delbert Peter Andrews, Oberkochen (DE); Nancy Hecker-Denschlag, Ulm (DE); Holger Matz, Unterschneidheim (DE); Christoph Hauger, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 1273 days.

(21) Appl. No.: 17/013,085

(22) Filed: Sep. 4, 2020

(65) Prior Publication Data

US 2021/0059857 A1    Mar. 4, 2021

(30) Foreign Application Priority Data

Sep. 4, 2019    (DE) ...................... 10 2019 123 742.4

(51) Int. Cl.
*A61F 9/007*    (2006.01)
*A61B 3/00*    (2006.01)
(Continued)

(52) U.S. Cl.
CPC ............ *A61F 9/007* (2013.01); *A61B 3/0008* (2013.01); *A61B 3/0025* (2013.01);
(Continued)

(58) Field of Classification Search
CPC ..... A61F 9/007; A61B 3/0008; A61B 3/0025; A61B 3/0041; A61B 3/12; A61B 3/13; A61B 34/10
See application file for complete search history.

(56) References Cited

U.S. PATENT DOCUMENTS 9,827,066 B2 *  11/2017  Abt .......................... A61B 3/13
2015/0173644 A1 *  6/2015  Ren ..................... A61F 9/00736
600/424

(Continued)

FOREIGN PATENT DOCUMENTS

WO    2019/244040 A2    12/2019

OTHER PUBLICATIONS

Muetze, K. et al, "ABC der Optik", 1972 Verlag Werner Dausien, Hanau/Main 1961, English translation of pp. 83 to 85, 7 pages.
(Continued)

*Primary Examiner* — Jing Rui Ou
(74) *Attorney, Agent, or Firm* — Walter Ottesen, P.A.

(57) ABSTRACT

An eye surgery surgical system includes a visualization device for visualizing the position of at least one trocar point for a trocar on the sclera of a patient's eye. The trocar serves to introduce a surgical instrument configured for surgical interventions on the fundus of the patient's eye into the patient's eye. The eye surgery surgical system also includes a computer unit which is configured to provide the position of the at least one trocar point to the visualization device. Here, the computer unit contains a trocar point computation routine configured to calculate the position of the at least one trocar point from the location of at least one surgical site in a model of the patient's eye and from geometric data relating to at least one surgical instrument introducible into the patient's eye through the trocar.

12 Claims, 5 Drawing Sheets

(51) Int. Cl.
    *A61B 3/12*     (2006.01)
    *A61B 3/13*     (2006.01)
    *A61B 34/10*    (2016.01)

(52) U.S. Cl.
    CPC ............. *A61B 3/0041* (2013.01); *A61B 3/12* (2013.01); *A61B 3/13* (2013.01); *A61B 34/10* (2016.02)

(56) References Cited

U.S. PATENT DOCUMENTS

| | | | | |
|---|---|---|---|---|
| 2016/0183779 | A1* | 6/2016 | Ren | A61B 90/20 351/246 |
| 2017/0035287 | A1* | 2/2017 | Ren | A61B 3/0058 |
| 2017/0280989 | A1* | 10/2017 | Heeren | A61B 1/01 |
| 2019/0388271 | A1 | 12/2019 | Abt | |

OTHER PUBLICATIONS

Translation and Office action of the German Patent Office dated Jun. 10, 2020 in German patent application 10 2019 123 742.4 on which a claim of priority is based.

* cited by examiner

EYE SURGERY SURGICAL SYSTEM AND COMPUTER IMPLEMENTED METHOD FOR PROVIDING THE POSITION OF AT LEAST ONE TROCAR POINT

CROSS REFERENCE TO RELATED APPLICATION

This application claims priority of German patent application no. 10 2019 123 742.4, filed Sep. 4, 2019, the entire content of which is incorporated herein by reference.

FIELD OF THE INVENTION

The invention relates to an eye surgery surgical system and a computer-implemented method for providing the position of at least one trocar point for a trocar on the sclera of a patient's eye, which serves to introduce at least one surgical instrument configured for surgical interventions on the fundus of the patient's eye into the patient's eye. Moreover, the invention relates to a computer program.

BACKGROUND OF THE INVENTION

Vitreoretinal surgery uses surgical instruments that are guided into the interior of a patient's eye through a trocar. By way of example, to carry out so-called retinal vein cannulation (RVC), cannulas with a shaft body are used, at the end of which a surgical tool in the form of a fine hollow needle, as a rule angled at an inclination angle with respect to the shaft body, is formed. The hollow needle allows medicaments to be introduced into retinal vessels, for example to break up coagulations. During this operation, the shaft body with the hollow needle is introduced into the interior of the patient's eye through a trocar which is inserted through the ring-shaped pars plana of the patient's eye, located between the outer edge of the retina and the ciliary body, in order to spare the sclera during surgery or to temporarily fix the instruments.

The supply of medicaments into a retinal vessel is only successful if the hollow needle enters the vessel at an angle of attack within a narrow tolerance range, with respect to the longitudinal direction of the vessel. If the angle of attack is too flat, the hollow needle cannot reach the lumen of the vessel. If the hollow needle is placed on the vessel at an angle of attack that is too steep, the region in which the end of the hollow needle is located in the lumen of the vessel will be very small. Then, even very small relative movements between hollow needle and fundus can lead to the hollow needle piercing through the vessel or slipping out of the vessel again.

However, should a hollow needle pierce through a retinal vessel or slip out of such a vessel, the retinal vessel, which is then perforated, bleeds into the vitreous humour of the patient's eye. Blood that has entered the vitreous humour can impair the surgeon's view of the fundus during an eye operation. Additionally, the perforation of a retinal vessel leads to medicaments introduced into the retinal vessel being promptly rinsed out of the latter again through the openings. A possible consequence is that the retinal vessel can no longer be treated correctly.

If a surgical instrument is introduced into the interior of a patient's eye through a stationary trocar, this reduces the number of degrees of freedom of movement with which the surgical tool of the surgical instrument can be moved in the interior of the patient's eye in relation to the number of degrees of freedom of movement of a freely movable surgical instrument.

Therefore, the region in the interior of the patient's eye intended to be operated on by means of the surgical instrument must already be considered when placing a trocar for the surgical instrument. This is because the angle of attack for a surgical tool of the surgical instrument with respect to a structure in the interior of the patient's eye, for example, a pointed cannula, a blade or a pair of scissors, can subsequently no longer be varied as desired.

In the case of surgical operations in the interior of a patient's eye, a surgeon often handles surgical instruments with a surgical tool at angles of attack with respect to structures in the interior of the patient's eye which are very inexpedient and therefore could cause complications. Often, it only becomes clear after placing the trocar that a planned intervention on the retina cannot be carried out because the surgical instrument introduced into the interior of the patient's eye through the trocar does not allow the angles of attack of the surgical tool of the surgical instrument required for the intervention.

This can be countered by keeping available a multiplicity of different surgical instruments which, given a position of the trocar, allow different angles of attack with respect to structures in the interior of the patient's eye. However, inserting and removing different surgical instruments through a placed trocar to find out which surgical instrument allows the surgical intervention to be carried out best lengthens the time required for the surgical intervention to be carried out. Moreover, keeping available and using different surgical instruments causes significant costs during procurement and operation.

There are also surgical instruments with hinges that allow the angle of attack of the surgical tool to be varied in the case of a surgical instrument guided into the interior of a patient's eye through a placed trocar. However, such surgical instruments are expensive to produce and can only be sterilized with great outlay, if at all.

If it turns out that it is not possible to carry out the planned surgical intervention in the interior of the patient's eye using the placed trocar, it is necessary to place the trocar anew. Particularly if use is made of further surgical instruments and auxiliary devices in the form of stands or robots, this requires a lot of time since the further surgical instruments may also have to be repositioned and, for instance, robots need to be realigned and programmed for the new so-called remote center of motion (RCM). Then, a patient inevitably experiences additional injury during the operation and the costs for carrying out the surgical intervention increase on account of the need for additional consumables, required in that state, and the lengthening of the duration of the operation.

US 2019/0388271, which has a later publication date, describes an eye surgery visualization system containing an ophthalmic surgical microscope and comprising a digital camera connected to the ophthalmic microscope. The interior of a patient's eye can be visualized by means of the ophthalmic surgical microscope. The digital camera serves to capture the outside of the patient's eye during ophthalmological surgery. The eye surgery visualization system has a display, by means of which both the interior of the patient's eye and its surroundings can be displayed to a surgeon at the same time.

SUMMARY OF THE INVENTION

It is an object of the invention to provide an eye surgery surgical system and a method for providing the position of at least one trocar point for a trocar on the sclera of a patient's eye, which facilitates optimized workflows in a surgical intervention in the interior of a patient's eye.

This object is achieved by the eye surgery surgical system for providing the position of at least one trocar point for a trocar on the sclera of a patient's eye.

An eye surgery surgical system of the invention includes a visualization device for visualizing the relative position of at least one trocar point for a trocar on the cornea of a patient's eye, which serves to introduce a surgical instrument configured for surgical interventions on the fundus of the patient's eye into the patient's eye, and includes a computer unit, which is configured to provide the position of the at least one trocar point to the visualization device. This computer unit contains a trocar point calculation routine, which is configured to calculate the position of the at least one trocar point from the location of at least one surgical site in a model of the patient's eye and from geometric data relating to at least one surgical instrument that is introducible into the patient's eye through a trocar.

A model of the patient's eye within the meaning of the invention can be a sphere or else an individual, patient-specific reproduction of the eyeball of a patient's eye. In particular, the model of an object within the meaning of the invention could be an average eye as per Gullstrand, as described, for instance, in ABC der Optik, Verlag Werner Dausien, Hanau/Main 1961, on pages 83 to 85. Here, for an "exact eye model" and a "simplified eye model", the optically effective surfaces, their curvature and spacing, and the refractive index of "optical elements" are specified, for which an imaging beam path corresponds, to a good approximation, to the natural conditions in the case of an average, healthy human with an emmetropic eye. By considering distances or curvatures specified in the "exact eye model" according to Gullstrand or in the "simplified eye model" not as specified parameters but as free parameters that are able to be fitted to a specific patient's eye, it is possible to describe a real patient's eye using such a model.

The eye surgery surgical system can contain a device for referencing the model of the patient's eye to the patient's eye. This facilitates visualizing the correct position of the calculated position of the trocar on the patient's eye for a surgeon and/or displaying the model of the patient's eye overlaid on an image of the patient's eye captured by an image capturing device.

It is advantageous if the trocar point calculation routine is configured to calculate the position of the at least one trocar point taking account of a posture of a surgeon that is practical from an ergonomic point of view for manipulating the surgical instrument within a surgical intervention. This makes it easier for the surgeon to work without tiring.

In particular, it is advantageous if the trocar point calculation routine is configured to calculate the position of the at least one trocar point while maximizing a distance of the surgical instrument from a region of critical tissue in the model of the patient's eye. This measure reduces the risk of complications in the case of a surgical intervention in the interior of the patient's eye.

It should be noted that the trocar point calculation routine can be configured to calculate a plurality of possible positions of trocar points, displayable by means of the visualization device, for a surgical instrument. Here, the trocar point calculation routine can be configured to calculate a plurality of possible positions of trocar points, displayable by means of the visualization device, for different surgical instruments.

In particular, the computer unit can be configured to provide a surgical instrument display function to the visualization device in order to identify trocar points belonging to a certain surgical instrument by means of the visualization device.

An advantageous embodiment of the invention provides for the trocar point calculation routine to be configured to calculate the position of the at least one trocar point by applying at least one mathematical optimization criterion. Here, provision can be made for the optimization criterion to take account of a surgery workflow.

By way of example, the optimization criterion can take account of, for example, a surgery workflow in which a plurality of equivalent surgical instruments with surgical tools are included in surgical planning, wherein it is taken into account that the surgical tools of the surgical instruments have different inclination angles $\beta$ with respect to a longitudinal axis of a shaft of the corresponding surgical instrument.

By way of example, provision can be made for the trocar point calculation routine to process a specified intended angle of attack $\alpha_{intended}$ of a surgical tool of the surgical instrument relative to the at least one surgical site for the calculation of the position of the at least one trocar point.

In particular, provision can be made for the trocar point calculation routine to process a specified tolerance range for the intended angle of attack $\alpha_{intended}$ of a surgical tool of the surgical instrument relative to the at least one surgical site for the calculation of the position of the at least one trocar point and specify a tolerance range, ascertained from the tolerance range for the intended angle of attack $\alpha_{intended}$ of the surgical tool, for a calculated position of the at least one trocar point.

As an alternative or in addition thereto, provision can be made for a treatment to be implemented at a plurality of spaced apart areas on the fundus of the patient's eye and for the trocar point calculation routine to take account of combinations of different surgical instruments with surgical tools, the inclination angles $\beta$ of which vary relative to the shaft of the surgical instrument, in order to determine a trocar point such that the surgical instruments ensure the required angle of attack $\alpha$ of the surgical tool with respect to the surgical site in the spaced apart areas on the fundus of the patient's eye through a single trocar arranged at the trocar point, at least within the scope of a certain tolerance range.

In the computer-implemented method according to the invention for providing the position of at least one trocar point for a trocar on the sclera of a patient's eye, which is used to insert at least one surgical instrument which is configured for surgical interventions on the fundus of the patient's eye into the patient's eye, the position of the at least one trocar point is calculated from the relative position of at least one surgical site in a model of the patient's eye and from geometric information about the at least one surgical instrument.

The invention also extends to a computer program with program code means for carrying out this method on a computer unit.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
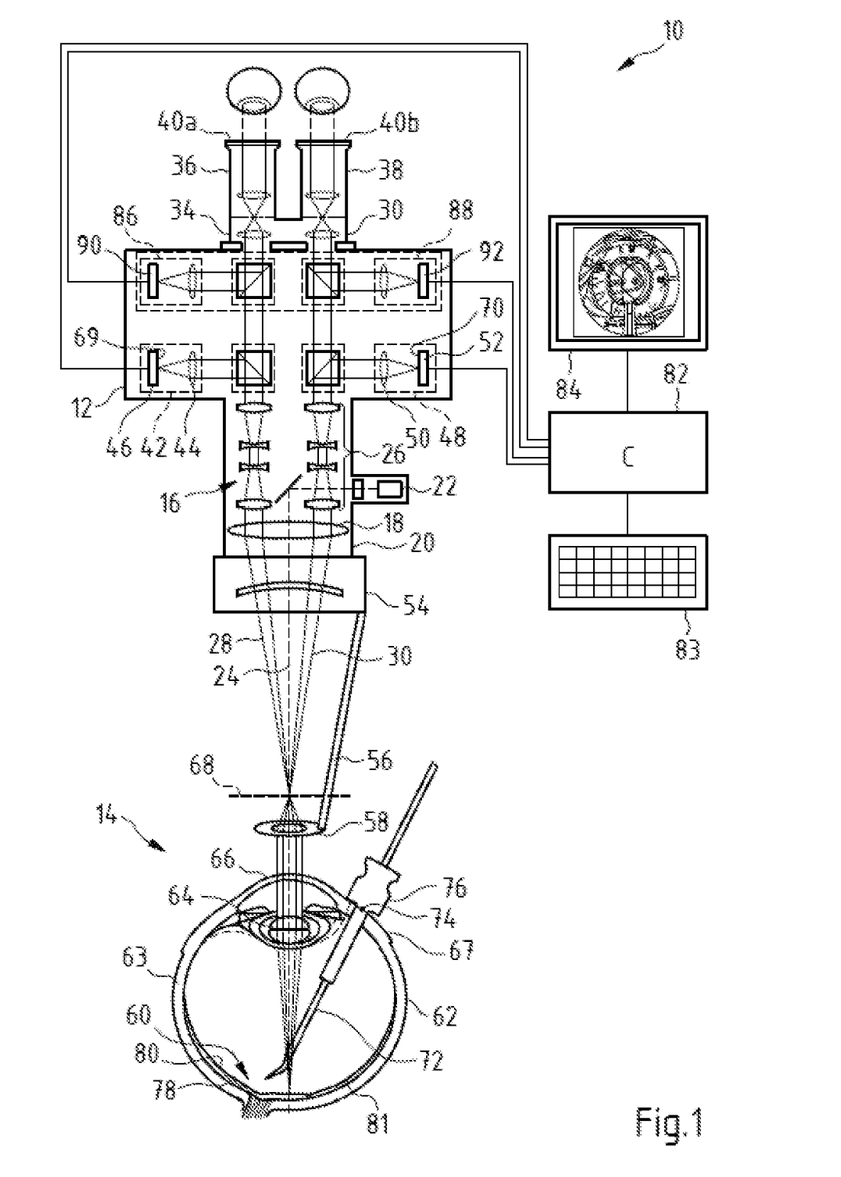
FIG. 1 shows an eye surgery surgical system with a patient's eye.

The eye surgery surgical system 10 shown in FIG. 1 contains a surgical microscope 12, which serves for the stereoscopic observation of an object region 14. The surgical microscope 12 comprises an imaging optical unit 16 with a microscope main objective system 18, the imaging optical unit being received in a main body 20. In the surgical microscope 12, there is an illumination device 22, which facilitates the illumination of the object region 14 with an illumination beam path 24, which passes through the microscope main objective system 18. The surgical microscope 12 has an afocal magnification system 26, through which a first stereoscopic partial observation beam path 28 and a second stereoscopic partial observation beam path 30 are guided. The surgical microscope 12 has a binocular tube 34 connected to an interface 32 of the main body 20, the binocular tube having a first eyepiece 36 and a second eyepiece 38 for a left and a right eye 40a, 40b of a surgeon. The microscope main objective system 18 in the surgical microscope 12 is traversed by the first stereoscopic partial observation beam path 28 and the second stereoscopic partial observation beam path 30. In the surgical microscope 12, there is a first image capturing device 42 with a first objective lens system 44 and with a first image sensor 46. The image capturing device 42 serves to capture image information from the first stereoscopic partial observation beam path 28. By means of a second image capturing device 48, image information from the second stereoscopic partial observation beam path 30 can be captured in the surgical microscope 12. The second image capturing device 48 has a second objective lens system 50 and contains a second image sensor 52.

An ophthalmoscopy attachment module 54 comprising an ophthalmoscopy loupe 58 that is received in an ophthalmoscopy loupe support 56 is connected to the surgical microscope 12. The ophthalmoscopy loupe 58 serves to image a surgical site 60 lying in the interior of a patient's eye 62, through the natural lens 64 and the cornea 66 of the latter, into an intermediate image plane 68, which is conjugate to the imaging plane 69 on the first image sensor 46 and to the imaging plane 70 on the second image sensor 52.

Arranged in the patient's eye 62 is a surgical instrument 72, which has been introduced into the interior of the patient's eye 62 through a trocar 76 which has been placed on a trocar point 74 in the sclera 63 in the region of the pars plana 67 of the patient's eye 62. By way of example, the surgical instrument 72 serves to introduce a medicament breaking up blood coagulation into a vessel 78, which extends along the fundus 80 of the patient's eye 62.

To be able to indicate to the surgeon the relative position of the trocar point 74 at which the trocar 76 can be placed in order to undertake a surgical intervention by means of the surgical instrument 72 in the surgical site 60, the eye surgery surgical system 10 has a computer unit 82, which comprises an input interface 83 and which is connected to the visualization device 84, embodied as a monitor, and to visualization devices 86, 88, which contain displays 90, 92.

The visualization device 84 facilitates the visualization of the relative position of the trocar point 74 in the object region 14 of the surgical microscope 12 in a three-dimensional image of the object region 14, which is calculated in the computer unit 82 by means of the image information captured by the first image capturing device 42 and the second image capturing device 48.

The displays 90, 92 of the visualization devices 86, 88 facilitate the display of display information in the first and second stereoscopic partial observation beam path 28, 30, overlaid on an image of the object region 14 perceivable in the binocular tube 34.

Figure 2:
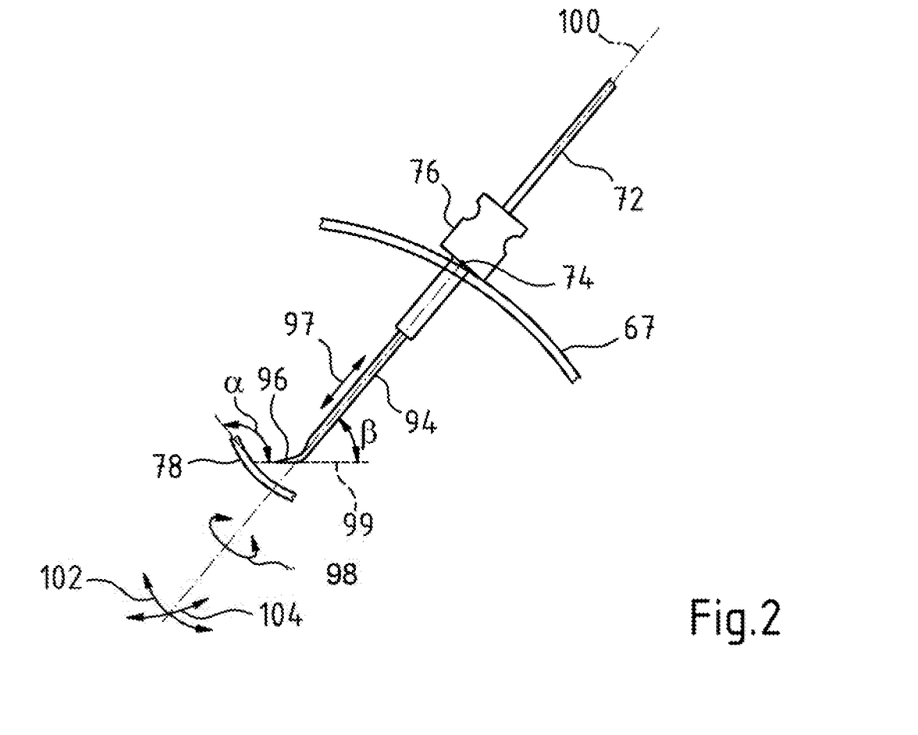
FIG. 2 shows a section of the patient's eye with a surgical instrument and with a trocar, which has been placed at the patient's eye at a trocar point.

FIG. 2 shows a section of the patient's eye 62 with the surgical instrument 72 and with the trocar 76, which is placed into the patient's eye 62 at the trocar point 74, the latter being able to be displayed by means of the visualization devices 84, 86, 88 in the eye surgery surgical system 10.

The surgical instrument 72 has a surgical tool 96 arranged on a shaft 94. It passes through the trocar 76 and can be moved in the latter in the direction of the double-headed arrow 97 and can be rotated about its longitudinal axis 100 in accordance with the double-headed arrow 98. Moreover, the trocar 76 allows the surgical instrument 72 to be pivoted about the trocar point 74 in a solid angle range related to the trocar point 74, in accordance with the double-headed arrows 102, 104. As a result of the trocar 76, the angle of attack α of the surgical tool 96 with respect to a vessel 78 can only be set by displacing the surgical instrument 72 in accordance with the directions represented by the double-headed arrows 97, 98, 102 and 104, with this however likewise altering the location of attack for the surgical tool 96 on the vessel 78. For a given location of the surgical site 60 in the patient's eye 62, the possible angle of attack α for the surgical tool 96 emerges from the geometry of the surgical instrument 72 and the relative position of the trocar point 74 for the trocar 76 in the pars plana 67 of the sclera 63 of the patient's eye 62.

Therefore, the computer unit 82 in the eye surgery surgical system 10 contains a trocar point calculation routine. For a surgical site 60 on a patient's eye 62 and for a surgical instrument 72 suitable for the surgical intervention, the trocar point calculation routine calculates a relative position, expedient for the surgical intervention, of a trocar point 74, at which a trocar 76 can be placed against the patient's eye 62, the trocar allowing the surgical instrument 72 to be inserted therethrough into the interior of the patient's eye 62 in such a way that the intervention in the vessel 78 can be implemented at an expedient angle of attack α for the intervention by means of the surgical tool 96 of the surgical instrument 72.

The surgical tool 96 of the surgical instrument 72, shown in FIG. 2, is a surgical tool which allows a variation of the orientation of the shaft 94 in relation to the surgical site 60 in the case in the same angle of attack α since, as a matter of principle, the surgical tool 96 can be rotated about the inclination axis 99 without the angle of attack α being altered in the process.

Therefore, as a matter of principle, there are a multiplicity of trocar points suitable for the planned surgical intervention for the specified angle of attack α of the surgical tool 96 of the surgical instrument 72, the trocar points lying on the curve on the surface of the sclera which emerges from the orientation variance of the corresponding surgical instrument, provided the curve points of this curve are arranged in the pars plana of the sclera.

By contrast, if a surgical instrument provides no variation of the orientation of its surgical tool with respect to the surgical site, the relative position of a trocar point suitable for the planned surgical intervention already emerges from the specified angle of attack α of the surgical tool 96 of the surgical instrument 72 with respect to the surgical site 60. All that remains here is the possibility of ascertaining a suitable penetration point of the sclera, that is, a penetration point located in the pars plana, within a possibly present tolerance.

It should be noted that the trocar point calculation routine can allow for the use of a certain surgical instrument selected by the surgeon not being possible at the surgical site of the surgical intervention in the patient's eye 62. This allows the surgeon to correct a plan of the surgical operation already during the planning phase.

Figure 3:
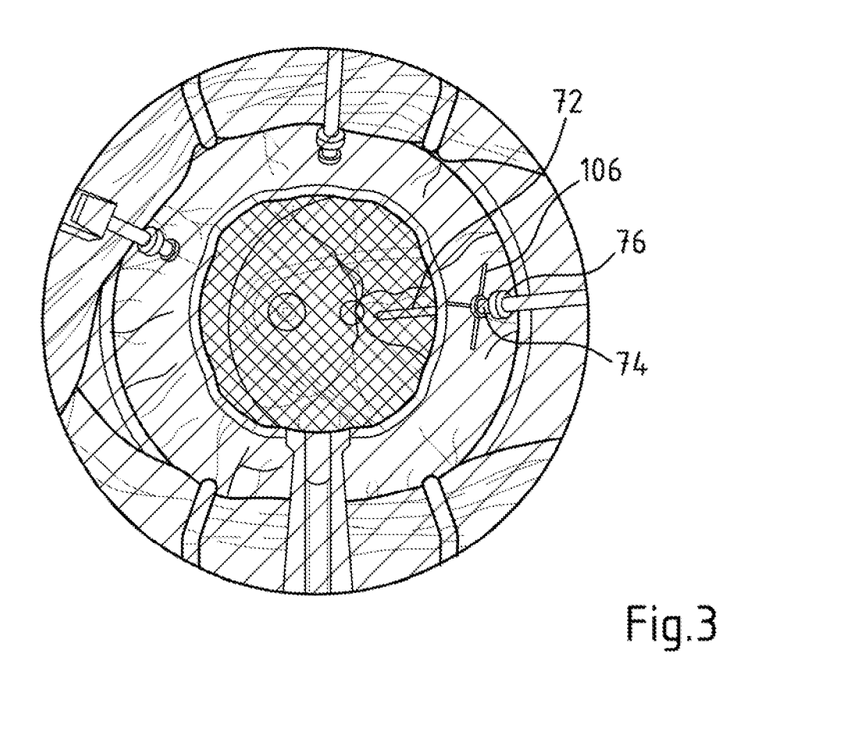
FIG. 3 shows a relative position of the trocar point visualized in the eye surgery surgical system.

FIG. 3 shows a relative position of the trocar point 74, visualized in the eye surgery surgical system 10 by means of a cross-shaped symbol 106. The relative position of the trocar point 74 is calculated in the computer unit 82 by means of the trocar point calculation routine. In the eye surgery surgical system 10, the relative position of the trocar point 74 on the pars plana 67 of the sclera 63 of the patient's eye 62 is displayed to a surgeon in the first and second eyepiece 36, 38, in a superposition as an image of the object region 14 identified in FIG. 1.

Figure 4:
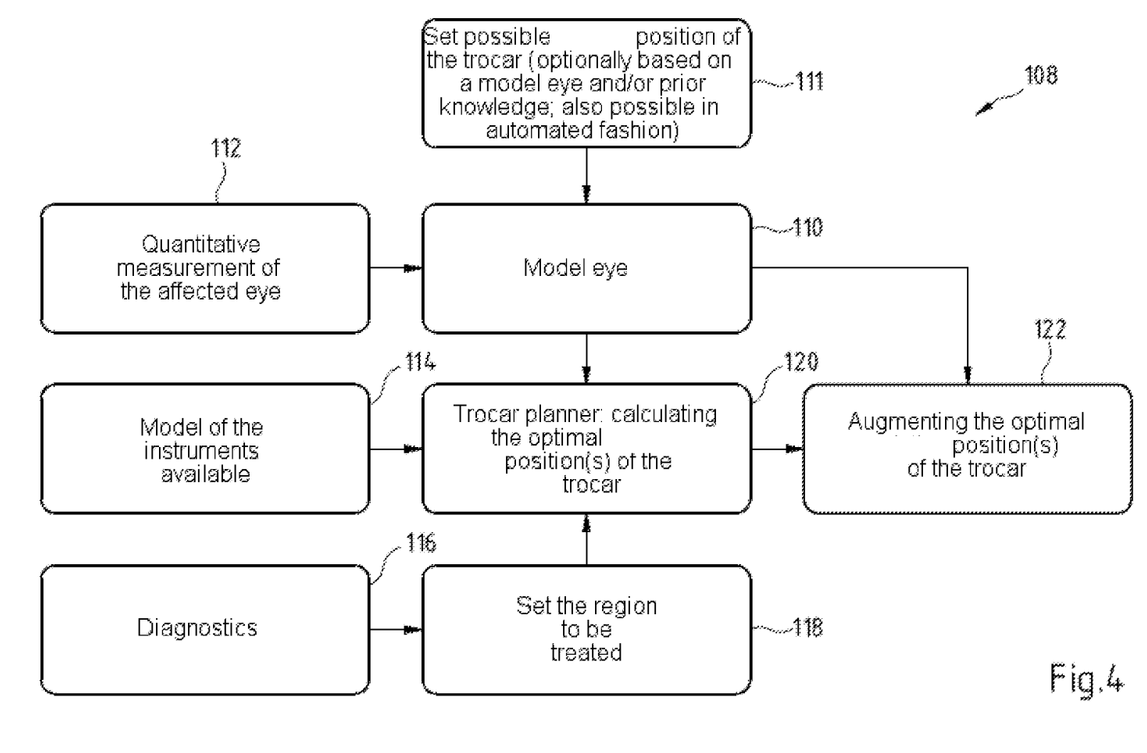
FIG. 4 shows a flowchart of a trocar point calculation routine, which is stored in a computer unit of the eye surgery surgical system.

FIG. 4 shows a flowchart 108 relating to a trocar point calculation routine, which is stored in a computer unit 82 of the eye surgery surgical system 10. By means of the trocar point calculation routine, the relative position of the trocar point 74 is calculated in the computer unit 82 from the relative position of at least one surgical site 60 in a model of the patient's eye and from geometric information relating to at least one surgical instrument 72 introducible into the patient's eye 62 through a trocar 76, which are ascertained in the trocar point calculation routine from a model relating to the surgical instrument 72.

The trocar point calculation routine in the computer unit 82 has an eye model ascertainment stage 110, which ascertains an eye model from measurement data 112 relating to the patient's eye 62 captured pre-surgery, which, by way of a comparison with image data supplied to the computer unit 82 from the image capturing devices 42, 48 in the surgical microscope 12, references this eye model to the patient's eye 62 arranged in the object region 14 of the surgical microscope 12. Here, data 111 about possible relative positions of a trocar 76 on a patient's eye 62 can be taken into account in the eye model ascertainment stage 110. Such data can be based, for example, on prior knowledge and/or on the ascertained model eye or else any other model eye.

It should be noted that, in a modified embodiment of the trocar point calculation routine, provision can be made for the eye model to be ascertained in the eye model ascertainment stage either exclusively or additionally from measurement data related to the patient's eye, which were captured during surgery. It should be noted, in particular, that measurement data for ascertaining an eye model of the patient's eye could be OCT data.

The eye model ascertained in the eye model ascertainment stage 110 comprises the sclera 63 shown in FIG. 1 and the retina 81, and the spatial relationship to one another.

Then, the trocar point calculation routine utilizes a data record 114 for surgical instrument models and a data record 116 concerning diagnostic data, from which a surgical site 60 in the patient's eye 62 is ascertained in a diagnostic data evaluation stage 118. Then, this spatial position of the trocar point 74 of the trocar 76 is calculated in a trocar position planning stage 120 for the ascertained eye model and the data record 114 for surgical instrument models and the information about the position of the surgical site 60 ascertained in the diagnostic data evaluation stage 118. Then, an image data record with image data is generated for the calculated spatial position of the trocar point 74 in an augmentation stage 122 of the trocar point calculation routine, the image data record containing the information about a position of the trocar 76, favorable for the planned surgical intervention, in an eye model of the patient's eye 62, which is referenced to the patient's eye 62 in the object region 14 of the surgical microscope 12 in the eye surgery surgical system 10. Consequently, the information about the sought-after favorable position of the trocar 76 can be displayed in the eye surgery surgical system 10 by the visualization devices 86, 88 in the surgical microscope 12 or the information can be displayed on the monitor of the visualization device 84.

Figure 5:
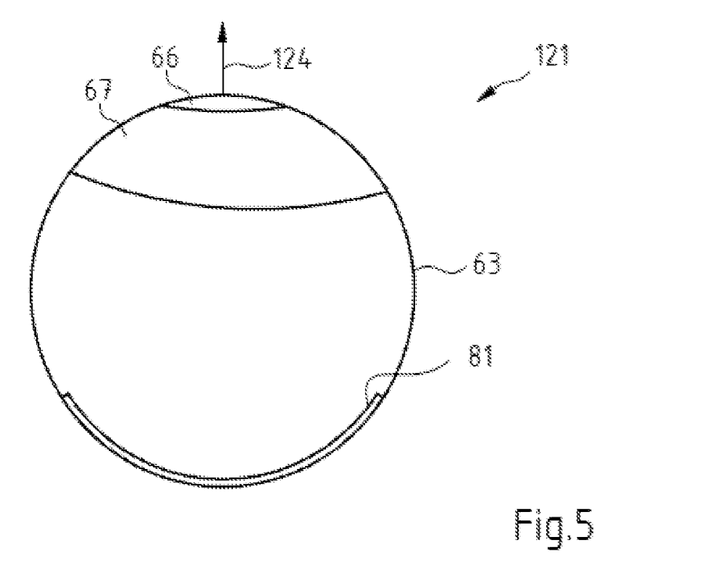
FIG. 5 shows a model of the patient's eye.

FIG. 5 shows a model 121 of the patient's eye 62 based on OCT data, in which model the patient's eye 62 is abstracted as a sphere that has an orientation corresponding to the viewing direction of the patient's eye 62, the orientation being identified by means of the arrow 124. The model 121 contains a spatial relationship of the retina 81 and the pars plana 67.

Figure 6:
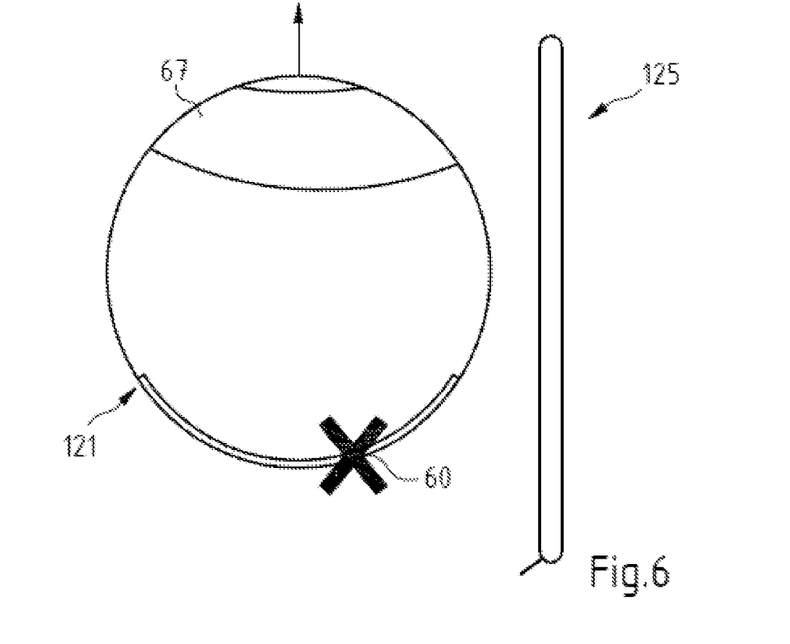
FIG. 6 shows the model of the patient's eye with a surgical site and with a model of the surgical instrument.

FIG. 6 shows the model 121 of the patient's eye 62 with a surgical site 60 and with a model 125 of the surgical instrument 72.

Figure 7:
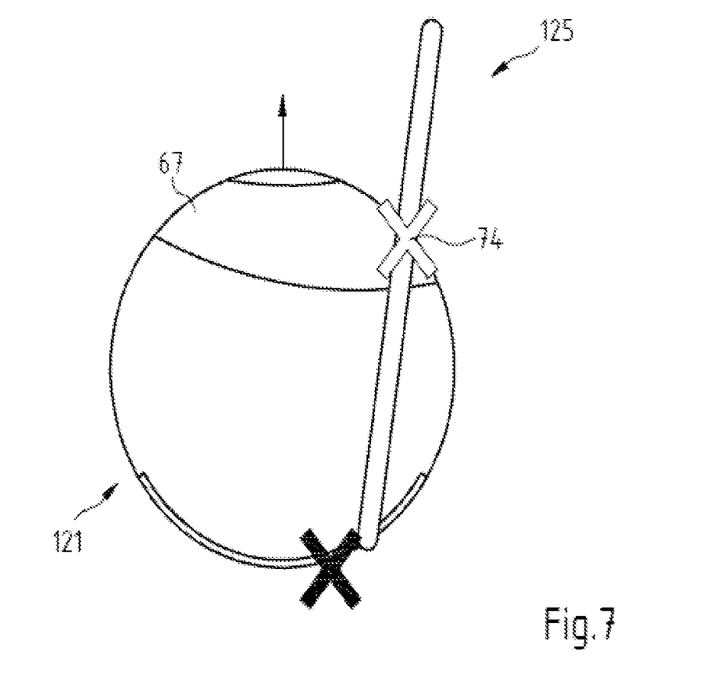
FIG. 7 shows the ascertainment of a trocar point in the model of the patient's eye on the basis of the model of the surgical instrument; and, FIG. 8 shows a section of the patient's eye with a further surgical instrument and with a trocar, which has been placed at the patient's eye at a trocar point.

In FIG. 7, the model 121 of the patient's eye 62 can be seen with the trocar point 74 calculated in the trocar position planning stage 120 and the model 125 of the surgical instrument 72.

Figure 8:
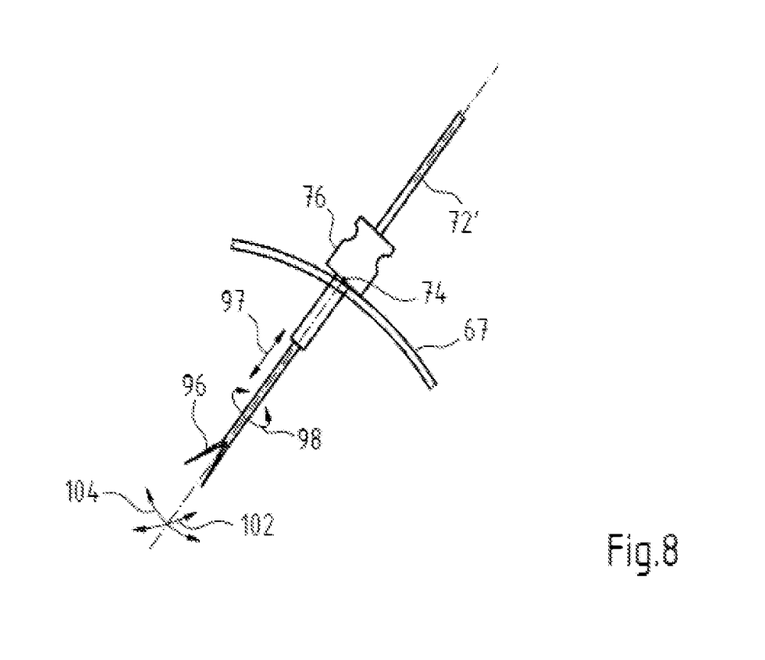

FIG. 8 shows a section of the patient's eye 62 with a further surgical instrument 72' and with a trocar 76, which has been placed at the patient's eye 62 at a trocar point 74. The surgical instrument 72' has a pair of scissors as surgical tool 96.

The surgical instrument 72' also passes through the trocar 76 and can be moved in the latter in the direction of the double-headed arrow 97 and can be rotated about its longitudinal axis 100 in accordance with the double-headed arrow 98. Moreover, the trocar 76 allows the surgical instrument 72 to be pivoted about the trocar point 74 in a solid angle range related to the trocar point 74, in accordance with the double-headed arrows 102, 104. The position of the trocar point 74 of the trocar 76 specifies the angle of attack α of the surgical tool 96 with respect to the vessel 78.

By means of the trocar point calculation routine described above on the basis of FIG. 4, the position of the trocar point 74 can be calculated in the computer unit 82 from the location of at least one surgical site 60 in a model of the patient's eye 62 and from geometric data relating to at least one surgical instrument 72' introducible into the patient's eye 62 through the trocar 76, which are ascertained in the trocar point calculation routine from a model relating to the surgical instrument 72'.

It should be noted that provision can be made of an alternative trocar point calculation routine to the trocar point calculation routine described above, the alternative routine including a plurality of equivalent surgical instruments with surgical tools in surgery planning, with it being taken into account that the surgical tools of the surgical instruments are configured for different angles of attack at the surgical site. It should be noted that, as an alternative or in addition thereto, the trocar point calculation routine can also take account of the fact that the angle of attack of the surgical tool of a surgical instrument is adjustable.

As an alternative or in addition thereto, the trocar point calculation routine can provide for a surgeon to be provided with choices for trocar points 74 in the eye surgery surgical system 10, at which trocar points 74 a trocar 76 can be placed. As an alternative or in addition thereto, the trocar point calculation routine can be configured to indicate to the surgeon the surgical instruments 72, 72' with the surgical tools 96 that are usable at certain trocar points 74. In particular, the trocar point calculation routine can be configured in such a way that particularly advantageous surgical instruments for carrying out the surgical intervention are displayed to the surgeon on the basis of an optimization criterion or that trocar points 74 take account of an ergonomically expedient posture of the surgeon by means of an optimization method or the trocar points are chosen in such a way that the risk of injuring critical tissue in a patient's eye 62 is minimized by maximizing the distance between the surgical tool 96 of the surgical instrument 72 and the critical tissue.

It should be noted that the trocar point calculation routine can be configured to specify combinations of the surgical tool 96 of a surgical instrument 72 and of the surgical site 60 in the patient's eye 62 as a set of points with trocar points 74, which can be considered for carrying out the planned surgical intervention and which, as a matter of principle, are of equal worth and from which the surgeon can then make a selection. Moreover, it should be noted that a trocar point calculation routine can additionally also provide for particularly advantageous trocar points to be ascertained from the trocar point calculation routine on the basis of an optimization method.

Moreover, it should be noted that if the treatment of a plurality of areas on the retina is required, this combination of the surgical tool 96 of a surgical instrument 72 and of the surgical site in the patient's eye 62 can be taken into account in a trocar point calculation routine in order to determine a trocar point 74 in such a way that the angles of attack of the surgical tool 96 of a surgical instrument 72 in respect of the surgical site 60 are located in a certain specified angular range or are minimal, for example. Here, the number of calculated trocar points can be reduced if the result of the calculation is not considered viable on account of a control criterion.

In summary, the following, in particular, should be noted: the invention relates to an eye surgery surgical system 10 comprising a visualization device 84, 86, 88 for visualizing the position of at least one trocar point 74 for a trocar 76 on the sclera 63 of a patient's eye 62, which serves to introduce a surgical instrument 72 configured for surgical interventions on the fundus of the patient's eye 62 into the patient's eye 62, and comprising a computer unit 82, which is configured to provide the position of the at least one trocar point 74 to the visualization device 84, 86, 88. Here, the computer unit 82 contains a trocar point calculation routine, which is configured to calculate the position of the at least one trocar point 74 from the location of at least one surgical site 60 in a model of the patient's eye 62 and from geometric information relating to at least one surgical instrument 72 that is introducible into the patient's eye 62 through a trocar 76.

It is understood that the foregoing description is that of the preferred embodiments of the invention and that various changes and modifications may be made thereto without departing from the spirit and scope of the invention as defined in the appended claims.

LIST OF REFERENCE SIGNS

10 First eye surgery surgical system
12 Surgical microscope
14 Object region
16 Imaging optical unit
18 Microscope main objective system
20 Main body
22 Illumination device
24 Illumination beam path
26 Afocal magnification system
28 First stereoscopic partial observation beam path
30 Second stereoscopic partial observation beam path
32 Interface
34 Binocular tube
36, 38 Eyepiece
40a, 40b Eye
42 First image capturing device
44 First objective lens system
46 First image sensor
48 Second image capturing device
50 Second objective lens system
52 Second image sensor
54 Ophthalmoscopy attachment module
56 Ophthalmoscopy loupe support
58 Ophthalmoscopy loupe
60 Surgical site
62 Patient's eye
63 Sclera
64 Natural lens
66 Cornea
67 Pars plana
68 Intermediate image plane
69 Imaging plane on the first image sensor
70 Imaging plane on the second image sensor
72, 72' Surgical instrument
74 Trocar point
76 Trocar
78 Vessel
80 Fundus of the patient's eye 62
81 Retina
82 Computer unit
83 Input interface
84, 86, 88 Visualization devices
90, 92 Display
94 Shaft
96 Surgical tool
97, 98 Double-headed arrow
99 Inclination axis
100 Longitudinal axis
102, 104 Double-headed arrow
106 Cross-shaped symbol
108 Flowchart
110 Eye model ascertainment stage
111 Data
112 Measurement data
114 Data record for surgical instrument models
116 Data record concerning diagnostic data 118 Diagnostic data evaluation stage
120 Relative trocar position planning stage
121 Model of the patient's eye
122 Augmentation stage
124 Arrow
125 Model of the surgical instrument

What is claimed is:

1. An eye surgery surgical system comprising:
a visualization device for visualizing a position of at least one trocar point for a trocar on the sclera of an eye of a patient, wherein the trocar is configured to permit introducing a surgical instrument into the eye of the patient, wherein the surgical instrument is configured for a surgical intervention on a fundus of the eye of the patient;
a computer unit configured to provide said position of said at least one trocar point to said visualization device; and,
said computer unit having a trocar point computation routine configured to calculate said position of said at least one trocar point from the location of at least one surgical site in a model of the eye of the patient and from geometric data directed to said surgical instrument introducible into the eye of the patient via said trocar.

2. The eye surgery surgical system of claim 1, further comprising a device for referencing the model of the patient's eye to the eye of the patient.

3. The eye surgery surgical system of claim 1, wherein said trocar point computation routine is configured to calculate the relative position of the at least one trocar point taking account of a posture of a surgeon that is practical from an ergonomic point of view for manipulating said surgical instrument during a surgical intervention.

4. The eye surgery surgical system of claim 1, wherein the trocar point computation routine is configured to calculate the position of said at least one trocar point while maximizing a distance of said surgical instrument from a region of critical tissue in the model of the patient's eye.

5. The eye surgery surgical system of claim 1, wherein said trocar point computation routine is configured to calculate a plurality of possible positions of trocar points, displayable by said visualization device, for said surgical instrument.

6. The eye surgery surgical system of claim 5, wherein the trocar point computation routine is configured to calculate the plurality of possible positions of trocar points, displayable by said visualization device, for different surgical instruments.

7. The eye surgery surgical system of claim 6, wherein the computer unit is configured to provide a surgical instrument display function to the visualization device to identify trocar points corresponding to a specific surgical instrument via said visualization device.

8. The eye surgery surgical system of claim 1, wherein the trocar point computation routine is configured to calculate the position of the at least one trocar point by applying at least one optimization criterion.

9. The eye surgery surgical system of claim 8, wherein said optimization criterion takes account of a surgery workflow in which a plurality of equivalent surgical instruments with surgical tools are included in a surgical planning, wherein account is taken that the surgical tools of the surgical instruments have different inclination angles ($\beta$) with respect to a longitudinal axis of a shaft of the surgical instrument and/or wherein a treatment is implemented at a plurality of spaced apart areas on the fundus of the eye of the patient and the trocar point computation routine takes account of combinations of different surgical instruments with surgical tools, the inclination angles ($\beta$) of the surgical tools varying relative to the shaft of the surgical instrument, in order to determine a trocar point such that the surgical instruments ensure the required angle of attack ($\alpha$) of the surgical tools with respect to the surgical site in the spaced apart areas on the fundus of the eye of the patient through a single trocar arranged at the trocar point, at least within the scope of a certain tolerance range.

10. The eye surgery surgical system of claim 1, wherein the trocar point computation routine processes a specified intended angle of attack ($\alpha_{intended}$) of a surgical tool of the surgical instrument relative to the at least one surgical site for the calculation of the position of the at least one trocar point.

11. The eye surgery surgical system of claim 10, wherein the trocar point computation routine processes a specified tolerance range for the intended angle of attack ($\alpha_{intended}$) of the surgical tool of the surgical instrument relative to the at least one surgical site for the calculation of the position of the at least one trocar point and specifies a tolerance range, ascertained from a tolerance range for the intended angle of attack ($\alpha_{intended}$) of the surgical tool, for a calculated position of the at least one trocar point.

12. An eye surgery surgical system comprising:
a surgical instrument configured for surgical intervention on a fundus of an eye of a patient;
a trocar configured to permit an introduction of said surgical instrument into the eye of the patient;
a visualization device for visualizing a position of at least one trocar point for said trocar on a sclera of the eye of the patient;
a computer unit configured to provide said position of said at least one trocar point to said visualization device; and,
said computer unit having a trocar point computation routine configured to calculate said position of said at least one trocar point from a location of at least one surgical site in a model of the eye of the patient and from geometric data directed to said surgical instrument introducible into the eye of the patient via said trocar.

* * * * *

UNITED STATES PATENT AND TRADEMARK OFFICE
CERTIFICATE OF CORRECTION

| | | |
|---|---|---|
| PATENT NO. | : 12,285,359 B2 | Page 1 of 1 |
| APPLICATION NO. | : 17/013085 | |
| DATED | : April 29, 2025 | |
| INVENTOR(S) | : C. Voigt et al. | |

It is certified that error appears in the above-identified patent and that said Letters Patent is hereby corrected as shown below:

In the Specification

In Column 6:
Lines 37 and 64: delete "attack a" and insert -- attack α -- therefor.

In Column 7:
Line 3: delete "a" and insert -- α -- therefor.

In Column 8:
Line 55: delete "a" and insert -- α -- therefor.

Signed and Sealed this
Eighteenth Day of November, 2025

John A. Squires
*Director of the United States Patent and Trademark Office*